United States Patent
Rana

(10) Patent No.: US 11,681,368 B2
(45) Date of Patent: Jun. 20, 2023

(54) METHOD, COMPUTER PROGRAM PRODUCT, CONTROL UNIT AND HEAD-MOUNTED DISPLAY FOR CONSERVING ENERGY IN AN EYE TRACKING SYSTEM

(71) Applicant: TOBII AB, Danderyd (SE)

(72) Inventor: Pravin Kumar Rana, Danderyd (SE)

(73) Assignee: TOBII AB, Danderyd (SE)

( * ) Notice: Subject to any disclaimer, the term of this patent is extended or adjusted under 35 U.S.C. 154(b) by 0 days.

(21) Appl. No.: 17/809,672

(22) Filed: Jun. 29, 2022

(65) Prior Publication Data

US 2023/0004219 A1 Jan. 5, 2023

(30) Foreign Application Priority Data

Jun. 30, 2021 (SE) .................... 2150851-0

(51) Int. Cl.
  *G06F 3/01* (2006.01)
  *G06V 40/18* (2022.01)
(52) U.S. Cl.
  CPC ............ *G06F 3/013* (2013.01); *G06V 40/193* (2022.01)
(58) Field of Classification Search
  CPC ..... G06F 3/013; G06F 3/0304; G06V 40/193; A61B 3/112; A61B 3/0025; A61B 3/0016; G02B 2027/0187; G02B 27/0093
  See application file for complete search history.

(56) References Cited

U.S. PATENT DOCUMENTS

| | | | |
|---|---|---|---|
| 2014/0320688 A1* | 10/2014 | Skogo | .................... H04N 5/378 348/222.1 |
| 2015/0092163 A1 | 4/2015 | Blixt et al. | |
| 2015/0199003 A1 | 7/2015 | Zhang et al. | |
| 2016/0274659 A1 | 9/2016 | Caraffi et al. | |
| 2016/0314349 A1* | 10/2016 | Eskilsson | ........... H04N 5/23245 |
| 2018/0103202 A1 | 4/2018 | Eskilsson et al. | |
| 2020/0382717 A1* | 12/2020 | Chiu | ................ H04N 5/232411 |
| 2021/0081038 A1 | 3/2021 | Sengelaub | |
| 2021/0173479 A1 | 6/2021 | Klingström | |

OTHER PUBLICATIONS

Swedish search report completed Mar. 4, 2022 regarding patent application SE 2150851-0.
Extended European search report completed Nov. 15, 2022 regarding patent application EP 22 18 0469.

* cited by examiner

*Primary Examiner* — Abhishek Sarma
(74) *Attorney, Agent, or Firm* — Kilpatrick Townsend & Stockton LLP

(57) ABSTRACT

An eye tracking system includes at least two cameras configured to register eye images of at least one eye. The system obtains eye images from at least one camera in a subset of the at least two cameras, determines a first pupil parameter based on a first eye image, and determines a second pupil parameter based on a second eye image. The system compares the first and second pupil parameters to obtain a test parameter and checks the test parameter against at least one operation criterion. Responsive to the checking, the system assigns a respective operation state to at least one camera in the subset. The operation state involves one of (A) operating the camera at a high frame rate, (B) operating the camera at a reduced frame rate being lower than high frame rate, (C) the camera being in a standby mode or (D) the camera being powered off.

19 Claims, 2 Drawing Sheets

METHOD, COMPUTER PROGRAM PRODUCT, CONTROL UNIT AND HEAD-MOUNTED DISPLAY FOR CONSERVING ENERGY IN AN EYE TRACKING SYSTEM

CROSS-REFERENCES TO RELATED APPLICATIONS

This application claims priority to Swedish Application No. 2150851-0, entitled "METHOD, COMPUTER PROGRAM PRODUCT, CONTROL UNIT AND HEAD-MOUNTED DISPLAY FOR CONSERVING ENERGY IN AN EYE TRACKING SYSTEM," filed on Jun. 30, 2021. The entire disclosure of the above-referenced application is incorporated herein by this reference.

TECHNICAL FIELD

The invention relates generally to power-efficient eye tracking. In particular, the present invention concerns a method for conserving energy in an eye tracking system that has at least two cameras configured to register eye images of at least one eye of a subject, a control unit configured to implement such a method, and a head-mounted display including the control unit. The invention also relates to a computer program product and a non-volatile data carrier.

BACKGROUND

To attain high quality and certainty, today's eye trackers usually employ more than one camera to record images of a subject's eyes. Further, each eye is typically illuminated by a plurality of light sources. Of course, this requires a comparatively large amount of energy. Especially in portable devices it is therefore important that the energy resources are not wasted.

US 2015/0199003 describes a solution for eye gaze detection based upon multiple cameras and/or light sources. The cameras and/or light sources are configured to provide eye gaze detection for a device display at different orientations, at different tilt angles, at different user positions, at different user distances, and so on. The document also shows a controller that selectively controls light source power and camera on/off state to provide images of the eye having sufficient quality for eye gaze detection and/or to conserve power.

Thus, a solution is known, where cameras and light sources are controlled in such a manner that the eye tracker's overall energy consumption is rendered relatively low. However, there is room for improvements of the efficiency.

SUMMARY

It is therefore an object of the present invention to offer an improved solution for controlling an eye tracking system in an energy-efficient manner.

According to one aspect of the invention, this object is achieved by a method for conserving energy in an eye tracking system containing at least two cameras configured to register eye images of at least one eye of a subject. The method is performed in at least one processor and involves obtaining eye images from at least one camera in a subset of the at least two cameras. A first pupil parameter is determined based on a first eye image of the eye images, and a second pupil parameter is determined based on a second eye image of the eye images. The first and second pupil parameters are compared to one another to obtain a test parameter. The test parameter is checked against at least one operation criterion; and in response thereto, a respective operation state is assigned to at least one camera in the subset of the at least two cameras. The operation state involves operating the camera at a high frame rate, operating the camera at a reduced frame rate being lower than the high frame rate, the camera being in a standby mode, or the camera being powered off.

This method is advantageous because it allows using only the best suited camera(s) at each point in time. Moreover, the cameras may be controlled to exclusively operate at the particular power level needed to attain a specified quality of the eye tracking.

According to one embodiment of this aspect of the invention, the subset of cameras contains a first camera, and the method involves: obtaining the first eye image captured by the first camera during a first time period; and obtaining the second eye image captured by the first camera during a second time period after the first time period. The test parameter includes a measure expressing a difference between the first and second eye images. Thus, it is straightforward to determine whether a quality of the image data registered by the first camera increases, decreases or remains essentially stable.

According to another embodiment of this aspect of the invention, the subset of cameras contains first and second cameras, and the method involves: obtaining the first eye image captured by the first camera during a first time period; and obtaining the second eye image captured by the second camera during the first time period. Here, the test parameter includes a measure expressing a difference between the first and second eye images. Thereby, it is straightforward to determine which camera that produces the best image data, or if both cameras provide essentially the same quality.

Preferably, the first and second cameras are configured to register the eye images of the same eye, however from different angles. Consequently, at least one of the cameras may produce high image data quality irrespective of the direction in which the subject aims his/her gaze.

According to yet another embodiment of this aspect of the invention, each of the first and second pupil parameters expresses a respective characteristics of the subject's pupil in terms of a pupil size and/or a pupil position. Namely, these are key characteristics to accomplish reliable eye tracking.

According to still another embodiment of this aspect of the invention, the pupil size is interpreted to designate a distance from a reference point in the first or second eye image, at which reference point a main optic axis of the camera and a normal of the pupil are parallel to one another, an indication of the pupil being partially occluded, or both. Thus, the pupil size, as such, is an important factor when establishing the image data quality.

According to another embodiment of this aspect of the invention, the method involves assigning the operation state to:
  operating the camera at the high frame rate, if the test parameter indicates that the eye image from the camera fulfills a first operation criterion;
  operating the camera at the reduced frame rate, if the test parameter indicates that the eye image from the camera fulfills a second operation criterion, however not the first operation criterion;

the standby mode, if the test parameter indicates that the eye image from the camera fulfills a third operation criterion, however neither the first nor the second operation criterion; and be powered off, if the test parameter indicates that the eye image from the camera does not fulfil any of the first, second or third operation criteria.

Thus, an adequate operation state may be assigned dynamically depending on which image data quality is provided by a particular camera at a particular point in time.

According to still another embodiment of this aspect of the invention, the first and second pupil parameters specify a respective number of glints detected in the first and second eye images respectively. The method further involves assigning the operation state to the at least one camera in the subset of the at least two cameras based on a number of glints detected in the first and second eye images respectively. Namely, in general, detecting more glints is better than detecting fewer glints, especially in the cornea. However, a shape of a pattern formed by the glints, and/or the shapes of the glints themselves may also be used as quality indicators.

According to a further embodiment of this aspect of the invention, the eye tracking system includes at least two light sources each of which is configured to project light towards the at least one eye of the subject such that corneal reflection data is generated in the eye images when the projected light is reflected by the eye. Here, the method involves selectively controlling the at least two light sources to be on or off based on the checking of the test parameter relative to the at least one operation criterion. As a result, exclusively those light sources may be activated that cause glints in an eye, which is currently being imaged. Naturally, this is beneficial from an energy-saving point-of-view.

According to another aspect of the invention, the object is achieved by a computer program product loadable into a non-volatile data carrier communicatively connected to at least one processor in an eye tracking system comprising at least two cameras configured to register eye images of at least one eye of a subject.

The computer program product contains software configured to, when the computer program product is run on the at least one processor, cause the at least one processor to: obtain eye images from at least one camera in a subset of the at least two cameras; determine a first pupil parameter based on a first eye image of the eye images; determine a second pupil parameter based on a second eye image of said eye images; compare the first and second pupil parameters to one another to obtain a test parameter; check the test parameter against at least one operation criterion; and in response thereto assign a respective operation state to at least one camera in the subset of the at least two cameras, which operation state involves: operating the camera at a high frame rate, operating the camera at a reduced frame rate being lower than the high frame rate, the camera being in a standby mode, or the camera being powered off. The advantages of this computer program product and non-volatile data carrier are apparent from the discussion above with reference to the proposed method.

According to yet another aspect of the invention, the above object is achieved by a control unit for conserving energy in an eye tracking system containing at least two cameras configured to register eye images of at least one eye of a subject. The control unit contains input and output interfaces and a processor. The input interface is configured to obtain eye images from at least one camera in a subset of the at least two cameras. The processor is configured to determine a first pupil parameter based on the first eye image of the eye images; and determine a second pupil parameter based on the second eye image of the eye images. The processor is further configured to compare the first and second pupil parameters to one another to obtain a test parameter; and check the test parameter against at least one operation criterion.

In response to the check, the processor is configured to assign a respective operation state to at least one camera in the subset of the at least two cameras, and forward the respective assigned operation state via the output interface to said at least one camera. The operation state involves operating the camera at a high frame rate, operating the camera at a reduced frame rate being lower than the high frame rate, the camera being in a standby mode, or the camera being powered off. The advantages of this control unit are apparent from the discussion above with reference to the proposed method.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DETAILED DESCRIPTION

Figure 1:
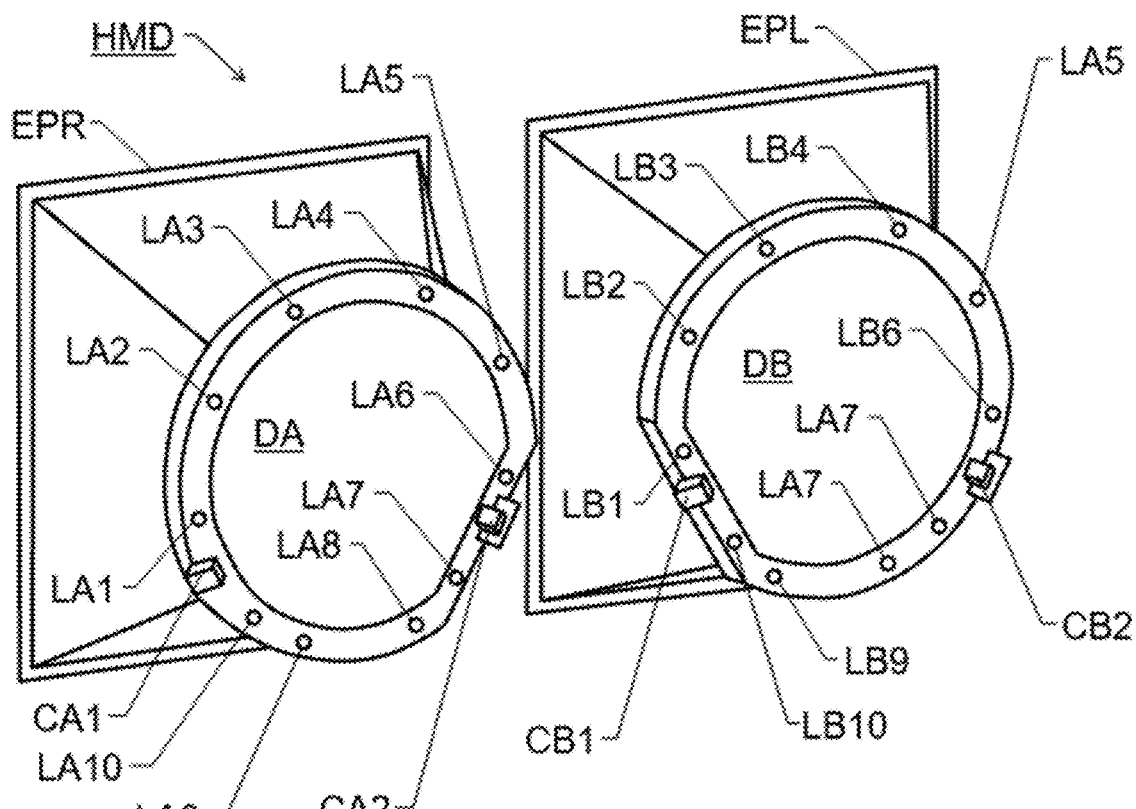
FIG. 1 shows an arrangement of cameras and light sources that are controllable according to one embodiment of the invention.

FIG. 1 shows an arrangement of cameras and light sources that are controllable according to one embodiment of the invention. Specifically, FIG. 1 exemplifies an arrangement suited to be included in a wearable design, for instance a head-mounted display (HMD) adapted for a virtual reality (VR), an augmented reality (AR) and/or a mixed reality (MR) application.

In FIG. 1, we see the arrangement from a back side in relation to a subject's eyes. Here, a right eyepiece EPR is equipped with a first display DA and a left eyepiece EPL has a second display DB.

The right eyepiece EPR also contains first and second cameras CA1 and CA2 respectively, which are configured to register eye images of the subject's right eye, and a first set of light sources LA1, LA2, LA3, LA4, LA5, LA6, LA7, LA8, LA9 and LA10 configured to project light towards the subject's right eye such that corneal reflection data is generated in eye images registered by the first and second cameras CA1 and CA2 when the projected light is reflected by the right eye. Analogously, the left eyepiece EPR contains third and fourth cameras CB1 and CB2 respectively, which are configured to register eye images of the subject's left eye, and a second set of light sources LB1, LB2, LB3, LB4, LB5, LB6, LB7, LB8, LB9 and LB10 configured to project light towards the subject's left eye such that corneal reflection data is generated in eye images registered by the third and fourth cameras CA1 and CA2 when the projected light is reflected by the left eye.

Preferably, as is apparent in FIG. 1, the first and second cameras CA1 and CA2 are configured to register the eye images of the right eye, however from different angles; and analogously, the third and fourth cameras CB1 and CB2 are configured to register the eye images of the left eye, however from different angles.

Figure 2:
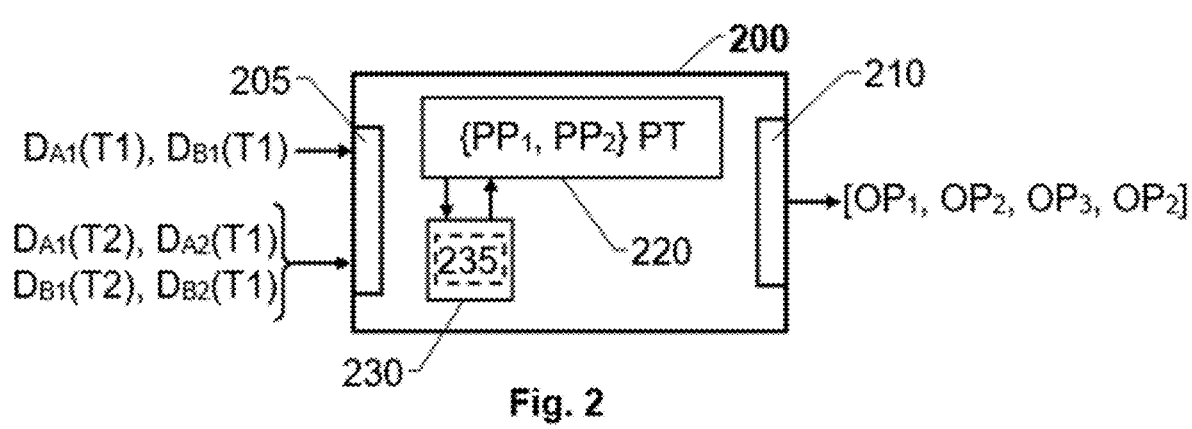
FIG. 2 shows a block diagram of a control unit according to one embodiment of the invention.

FIG. 2 shows a block diagram of a control unit 200 according to one embodiment of the invention. The control unit 200 is arranged to conserve energy in an eye tracking system including at least two cameras, such as the above-mentioned cameras CA1, CA2, CB1 and CB2, which are configured to register eye images of at least one eye of a subject.

The control unit 200 contains a processor 220, input and output interfaces 205 and 210 respectively, and a memory unit 230. The input interface 205 is configured to obtain eye images from at least one camera in a subset of the at least two cameras. For example, as illustrated by the examples of eye images in FIGS. 3a and 3b, the input interface 205 may obtain a first eye image DA1 (T1) of a subject's eye, which first eye image DA1 (T1) has been captured by the first camera CA1 during a first time period T1, and a second eye image DA2 (T1) of the subject's eye, which second eye image DA2 (T1) has been captured by the second camera CA2 during the first time period T1.

The input interface 205 may obtain a first eye image DA1 (T1) of a subject's right eye, which first eye image DA1 (T1) has been captured by a first camera CA1 during the first time period T1, and the second eye image DA2 (T1) depicts the subject's right eye, which second eye image DA2 (T1) has been captured by a second camera CA2 during the first time period T1.

Alternatively, the input interface 205 may obtain the first eye image DB1 (T1) of the subject's left eye, which first eye image DB1 (T1) has been captured by a third camera CB1 during the first time period T1, and the second eye image DB2 (T1) depicts the subject's left eye, which second eye image DB2 (T1) has been captured by a fourth camera CB2 during the first time period T1.

The processor 220 is configured to determine a first pupil parameter PP1 based on the first eye image DA1 (T1) or DB1 (T1), and determine a second pupil parameter PP2 based on the second eye image DA1 (T2) or DB2 (T1). The processor 220 is further configured to compare the first and second pupil parameters PP1 and PP2 to one another to obtain a test parameter PT.

According to one embodiment of the invention, the test parameter PT contains a measure expressing a difference between the first and second eye images DA1 (T1) (or DB1 (T1)) and DA1 (T2) (or DB2 (T1)) respectively.

Moreover, the processor 220 is configured to check the test parameter PT against at least one operation criterion. For example, if the eye tracking system is performing pupil tracking, the first and second pupil parameters PP1 and PP2 may describe respective pupil sizes, respective pupil motions and/or respective directions in which the pupil moves. In this disclosure, the term "pupil size" is understood to designate a total area covered by the pupil in an eye image, e.g. DA1 (T1), or DB1 (T1), DA1 (T2) or DB2 (T1). Hence, for example, the "pupil size" is not equivalent to a pupil diameter, or a pupil radius.

The at least one operation criterion may here be as follows. As long as the subject's eye pupil is fully visible in a field of view of the first camera CA1, the second camera CA2 shall be powered off, or at least be placed in a standby mode.

However, if the processor 220 determines, for example based on a visibility and movement direction of the subject's eye pupil, that the pupil moves toward a field of view of the second camera CA2, the processor 220 assigns such operation states to the first and second cameras CA1 and CA2 that the first camera CA1 is powered off, or at least be placed in the standby mode, and the second camera CA2 is activated. Preferably, during a transition phase, when the pupil might be fully visible in both the first and second cameras CA1 and CA2, both cameras are active and produce gaze signals, and/or other eye-tracking related signals.

Generally, according to the invention, the processor 220 is configured to compare the first and second pupil parameters PP1 and PP2 to one another to obtain a test parameter, and check the test parameter against an operation criterion. In response thereto, in turn, the control unit 220 is configured to assign a respective operation state to at least one camera in a subset of at least two cameras of the eye tracking system. The respective operation state OP1, OP2, OP3 or OP4 may involve: operating the camera at a high frame rate, operating the camera at a reduced frame rate being lower than the high frame rate, the camera being in a stand by mode, or the camera being powered off.

The output interface 210 is configured to forward the respective assigned operation state to each camera whose operation state is to be altered, i.e. CA1, CA2, CB1 and/or CB2.

Figures 3A, 3B:
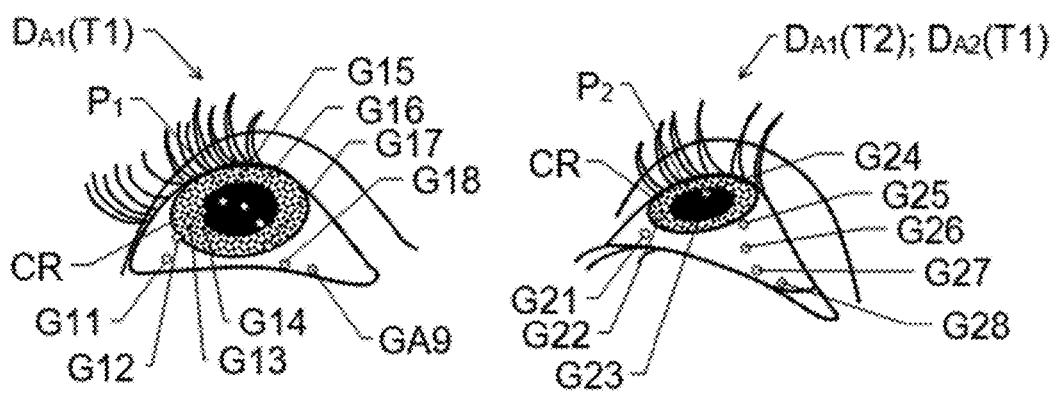
FIGS. 3a, 3b show examples of eye images of a subject according to one embodiment of the invention.

According to one embodiment of the invention as illustrated by the examples of eye images in FIGS. 3a and 3b, the control unit 220 obtains a first eye image Dai (T1), for example of the subject's right eye, captured by the first camera CA1 during a first time period T1; and obtains a second eye image $D_{A1}$ (T2) captured by the first Camera CA1 during a second time period T2 after the first time period T1. Here, the test parameter PT contains a measure expressing a difference between the first and second eye images $D_{A1}$ (T1) and $D_{A1}$ (T2). For example, the difference may relate to a difference in pupil information between the two images, such as a difference in pupil shape, e.g. the pupil P1 being more circular in the first eye image $D_{A1}$ (T1) and the pupil P2 being more oval in the second eye image $D_{A1}$ (T2), and/or the pupil P1 being at a first position relatively close to being in line with a main optic axis of the first camera CA1 in the first eye image $D_{A1}$ (T1) and the pupil P2 being at a second position further off from the main optic axis of the first camera CA1 in the second eye image $D_{A1}$ (T2).

Alternatively, the first eye image DB1 (T1) may depict the subject's left eye and be captured by the third camera CB1 during the first time period T1; and the second eye image DB1 (T2) may depict the subject's left eye and be captured by the third camera CB1 during the second time period T2 after the first time period T1.

This means that the first and second pupil parameters PP1 and PP2 may express a respective characteristics of the subject's pupil in terms of a pupil size and/or a pupil position in the eye image. Here, the test criterion is such that a larger pupil P1 is favored over a smaller pupil P2 because the former is interpreted to have been registered by a camera having a more favorable angular relationship to the normal of the pupil P1.

The control unit 220 may be configured to interpret the pupil size to designate a distance from a reference point in the eye image where a main optic axis of the camera and a normal of the pupil are parallel to one another. Here, a smaller pupil P2 is deemed to be more remote from the reference point than a larger pupil P1. Of course, the pupil's size in a recorded image may also be reduced because the pupil is partially occluded, for example because it is covered by an eyelid, and/or because the eye's angle toward the camera is very large. The control unit 220 is preferably also configured to interpret a smaller pupil size as a pupil being partially occluded. In any case, the test criterion is such that a closer/less occluded pupil is favored over a more distant/occluded ditto.

According to one embodiment of the invention, the control unit 220 is specifically configured to determine the pupil position based on a shape of the pupil $P_1$, $P_2$. Namely, the smaller the angle is between a main optic axis of the camera and the normal of the pupil, the more circular the pupil will be imaged, and vice versa. Here, the test criterion is such that a more circular pupil $P_1$ is favored over a less circular ditto.

Namely, an eye looking more away from the camera is depicted with a pupil shape being more oval, or "thinner", than what an eye looking less away from the camera is depicted. Thus, the overall pupil size will be smaller in the former case than in the latter. Ideally, a subject who is looking straight into the camera will show a maximum pupil size, i.e. that of a pupil P1 being depicted with a roughly circular shape.

Typically, in an HMD implementation, the pupil shape at large angles affect the pupil size much more than the actual change in distance between the camera and the pupil.

It is typically advantageous to first determine the pupil position in the image, and then determine the pupil size and/or shape as a basis for assigning an operation state to a particular camera, such as turning it on or off. In general, it is more difficult to accurately determine gaze data if the angle between the camera's main optic axis and the normal of the pupil P2 is large. Therefore, a camera having a small angle between the camera's main optic axis and the normal of the pupil P1 will be favored over a camera having a larger angle between the camera's main optic axis and the normal of the pupil P2. In other words if the angular difference between an active camera's main optic axis and the normal of the pupil P2 becomes too large, the strategy is to turn off/reduce the contribution from this camera, and instead turn on/increase the contribution from one or more other cameras depicting the same eye.

Above, the "pupil position" refers to a two-dimensional coordinate in the respective eye image. Moreover, the distance difference of interest is the distance difference between the pupil positions in the eye images, for example represented by the above-mentioned distance to the reference point in the eye image, where a main optic axis of the camera and a normal of the pupil are parallel to one another.

However, the distance difference between the pupil to the camera is less interesting. Preferably, namely, the cameras form part of an HMD, which basically remains static relative to the subject's eyes during operation, and therefore also the distances to the cameras are static in relation to the eye. Consequently, in such an HMD environment, each camera may determine an approximate location where the subject is looking only by identifying the pupil position in an eye image.

For example, the pupil position of the eye in the first eye image $D_{A1}$ (T1) or DB1 (T1) may be compared to the pupil position in the second eye image $D_{A1}$ (T2), DA2 (T1), DB1 (T2) or DB2 (T1), captured by the same camera during the second time period T2, or by another camera during the same time period T1.

Alternatively, the pupil position in the first eye image $D_{A1}$ (T1) or DB1 (T1) may be compared to a previously known pupil position, e.g. a reference image when the subject is looking straight into the camera in question CA1 or CB1 respectively.

As yet an alternative, the pupil position in the first image $D_{A1}$ (T1) or DB1 (T1) may be compared to a previously known pupil position of when the subject is looking in another well-defined direction, for instance straight ahead.

If more than two operation states are employed, it may be advantageous to assign an operation state to a particular camera according to a hierarchical principle in relation to different operation criteria. For example, this may involve operating the camera at the high frame rate, if the test parameter PT indicates that the eye image from the camera fulfills a first operation criterion. If the test parameter PT indicates that the eye image from the camera fulfills a second operation criterion, however not the first operation criterion, the camera may be operated at the reduced frame rate, i.e. below the high frame rate. Further, if the test parameter PT indicates that the eye image from the camera fulfills a third operation criterion, however neither the first nor the second operation criterion, the camera may be placed in the standby mode. Finally, if the test parameter PT indicates that the eye image from the camera does not fulfil any of the first, second or third operation criteria, the camera may be powered off.

FIGS. 3a and 3b also illustrate examples of how glints may occur in an eye of a subject according to one embodiment of the invention, for instance as depicted by the first and second cameras CA1 and CA2 respectively.

In FIG. 3a, nine glints are visible in the form of G11, G12, G13, G14, G15, G16, G17, G18 and G19, and in FIG. 3b eight glints are visible in the form of G21, G22, G23, G24, G25, G26, G27 and G28. According to one embodiment of the invention, the first and second pupil parameters PP1 and PP2 specify the respective number of glints, i.e. here nine and eight respectively, the control unit 220 is configured to assign the operation state, e.g. OP1, OP2, OP3 or OP4 to the at least one camera in the subset of the at least two cameras, here CA1 or CA2, based on the number of glints detected in the first and second eye images respectively. Here, the test criterion is such that a larger number of detected glints is favored over a smaller ditto. Thus, the first camera CA1 is favored over the second camera CA2.

According to embodiments of the invention, the operation state may also be assigned at higher precision and/or on alternative bases. For example, the first and second pupil parameters PP1 and PP2 may specifically express a respective number of detected glints in the cornea CR because corneal glints are more useful than for example glints in the sclera. Therefore, the test criterion may here be such that a larger number of corneal glints is favored over a smaller ditto. Again, in the example illustrated in FIGS. 3a and 3b, this means that the first camera CA1 is favored over the second camera CA2. Thus, a higher number of glints on or in the vicinity of the pupil P1, P2 is preferred.

Alternatively, or additionally, a shape of a pattern formed by the glints, and/or the shapes of the glints themselves may be used as quality indicators. Here, the test criterion may be such that a high similarity between the pattern formed by the glints and the pattern formed by the light sources is favored over a low similarity. Analogously, less distorted the glints relative to the shape of the light sources, are favored over more distorted ditto.

Returning again to FIG. 2, according to one embodiment of the invention, the control unit 200 is configured to selectively control at least one light source in the first set of light sources LA1, LA2, LA3, LA4, LA5, LA6, LA7, LA8, LA9 and LA10; and at least one light source in the second set of light sources LB1, LB2, LB3, LB4, LB5, LAB, LB7, LB8, LB9 and LB10 to be on or off based on the checking of the test parameter PT against the at least one operation criterion. Namely, this may save large amounts of energy, especially since the cameras registering eye images of the eye being illuminated by the light sources in question may be temporarily switched off as described above. For instance, if the light sources are near-IR LEDs, each light source may consume 8 mW. Consequently, by powering off a complete set of light sources, in total 8 mW×10=80 mW can be saved.

If the eye tracking system is performing gaze tracking and/or tracks eye movements, it is advantageous to track a gaze ray direction, and based thereon, dynamically control a power state of all the light sources per eye, i.e. the first set of light sources LA1, LA2, LA3, LA4, LA5, LA6, LA7, LA8, LA9 and LA10; and the second set of light sources LB1, LB2, LB3, LB4, LB5, LB6, LB7, LB8, LB9 and LB10 respectively.

Furthermore, knowledge of an eye movement state such as whether the eye is in fixation/saccade state and information about which camera that currently has the eye in its field of view, may be used to control the power state of the light sources in the first and second sets.

It is generally advantageous if the control unit 200 shown in FIG. 2 is configured to effect the above-described procedure in an automatic manner by executing a computer program 235. Therefore, the control unit 200 may include a memory unit 230, i.e. non-volatile data carrier, storing the computer program 235, which, in turn, contains software for a processor 220 in the control unit 200 execute the actions mentioned in this disclosure when the computer program 235 is run on the processor 220.

Figure 4:
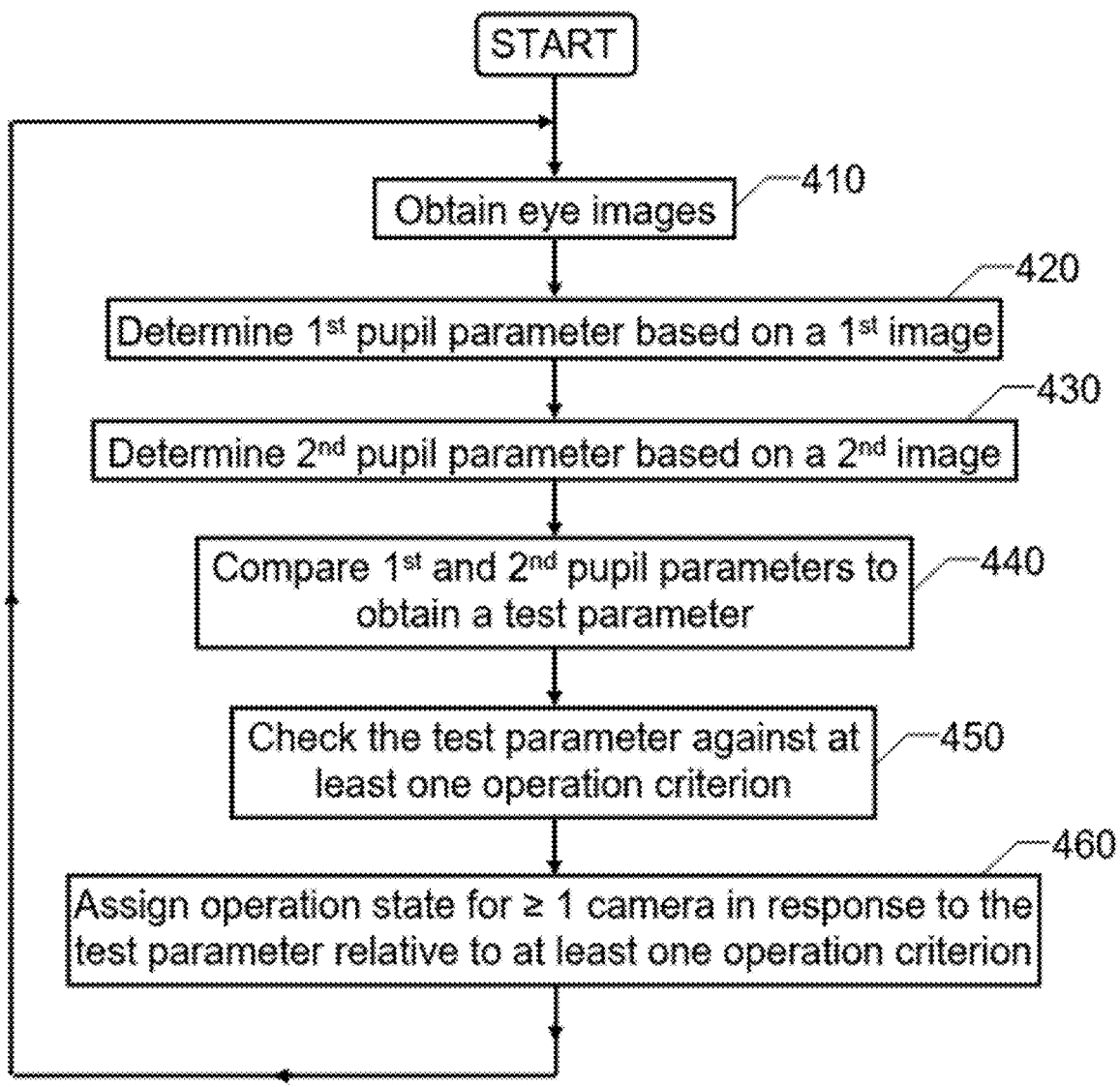
FIG. 4 illustrates, by means of a flow diagram, the general method according to the invention.

In order to sum up, and with reference to the flow diagram in FIG. 4, we will now describe the general method according to the invention for conserving energy in an eye tracking system that includes at least two cameras being configured to register eye images of at least one eye.

In a first step 410, eye images are obtained from at least one camera in a subset of the at least two cameras of the eye tracking system.

In subsequent steps 420 and 430, first and second pupil parameters $PP_1$ and $PP_2$ are determined based on first and second eye images respectively.

Thereafter, in a step 440, the first and second pupil parameters are compared to one another to obtain a test parameter; and in a following step 450, the test parameter is checked against at least one operation criterion.

In response to this checking, a step 460 assigns a respective operation state to the at least one camera in the subset of said at least two cameras. The operation state may involve: operating the camera at a high frame rate, operating the camera at a reduced frame rate being lower than the high frame rate, the camera being in a standby mode, or the camera being powered off. Naturally, the assigning of the respective operation state may involve turning a camera on to operate at the high frame rate or the reduced frame rate if the camera in question is turned off when entering step 460. Subsequently the procedure loops back to step 410.

All of the process steps, as well as any sub-sequence of steps, described with reference to FIG. 4 above may be controlled by means of at least one programmed processor. Moreover, although the embodiments of the invention described above with reference to the drawings comprise processor and processes performed in at least one processor, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

Variations to the disclosed embodiments can be understood and effected by those skilled in the art in practicing the claimed invention, from a study of the drawings, the disclosure, and the appended claims.

The term "comprises/comprising" when used in this specification is taken to specify the presence of stated features, integers, steps or components. The term does not preclude the presence or addition of one or more additional elements, features, integers, steps or components or groups thereof. The indefinite article "a" or "an" does not exclude a plurality. In the claims, the word "or" is not to be interpreted as an exclusive or (sometimes referred to as "XOR"). On the contrary, expressions such as "A or B" covers all the cases "A and not B", "B and not A" and "A and B", unless otherwise indicated. The mere fact that certain measures are recited in mutually different dependent claims does not indicate that a combination of these measures cannot be used to advantage. Any reference signs in the claims should not be construed as limiting the scope.

It is also to be noted that features from the various embodiments described herein may freely be combined, unless it is explicitly stated that such a combination would be unsuitable.

The invention is not restricted to the described embodiments in the figures but may be varied freely within the scope of the claims.

What is claimed is:

1. A method for conserving energy in an eye tracking system comprising at least two cameras configured to register eye images of at least one eye of a subject, wherein the method is performed in at least one processor and comprises:
   obtaining eye images from at least one camera in a subset of the at least two cameras;
   determining a first pupil parameter based on a first eye image of the eye images;
   determining a second pupil parameter based on a second eye image of the eye images;
   comparing the first pupil parameter and the second pupil parameter to one another to obtain a test parameter;
   checking the test parameter against at least one operation criterion; and in response to checking the test parameter against the at least one operation criterion, assigning a respective operation state to at least one camera in the subset of the at least two cameras, wherein the operation state involves one of: (A) operating the camera at a high framerate if the test parameter indicates that the eye image from the camera fulfills a first operation criterion, (B) operating the camera at a reduced frame rate being lower than high frame rate if the test parameter indicates that the eye image from the camera fulfills a second operation criterion but not the first operation criterion, (C) the camera being in a standby mode if the test parameter indicates that the eye image from the camera fulfills a third operation criterion but neither the first operation criterion nor the second operation criterion, or (D) the camera being powered off if the test parameter indicates that the eye image from the camera does not fulfill any of the first operation criterion, the second operation criterion, or the third operation criterion.

2. The method of claim 1, wherein the subset contains a first camera, the method further comprising:
   obtaining the first eye image captured by the first camera during a first time period; and
   obtaining the second eye image captured by the first camera during a second time period after the first time period,
   wherein the test parameter comprises a measure expressing a difference between the first eye image and the second eye image.

3. The method of claim 1, wherein the subset contains a first camera and a second camera, the method further comprising:
   obtaining the first eye image captured by the first camera during a first time period; and
   obtaining the second eye image captured by the second camera during the first time period,
   wherein the test parameter comprises a measure expressing a difference between the first eye image and the second eye image.

4. The method of claim 3, wherein the first eye image and the second eye image are images of the same eye of the subject; and
   wherein the first camera is configured to register the first eye image from a first angle relative to the same eye and the second camera is configured to register the second eye image from a second angle different from the first angle relative to the same eye.

5. The method of claim 1, wherein each of the first pupil parameter and the second pupil parameter expresses respective characteristics of a pupil of a subject in terms of one or more of a pupil size or a pupil position.

6. The method of claim 5, further comprising assigning the respective operation state to the at least one camera in the subset of the at least two cameras based on a shape of the pupil of the subject.

7. The method of claim 5, further comprising interpreting the pupil size to designate one or more of:
   a distance from a reference point in the first eye image or the second eye image where a main optic axis of the camera and a normal of the pupil of the subject are parallel to one another, or
   an indication of the pupil being partially occluded.

8. The method of claim 1, wherein each of the first pupil parameter and the second pupil parameter specifies a respective number of glints detected in the first eye image and the second eye image; and
   wherein the method further comprises assigning the operation state for the at least one camera in the subset of the at least two cameras based on the respective number of glints detected in the first eye image and the second eye image.

9. The method of claim 1, wherein the eye tracking system further comprises at least two light sources each of which is configured to project light towards the at least one eye of the subject such that corneal reflection data is generated in the eye images when the projected light is reflected by the eye; and
   wherein the method further comprises selectively controlling the at least two light sources to be on or off based on the checking of the test parameter against the at least one operation criterion.

10. A non-transitory computer readable medium comprising program code that, when executed by at least one processor in an eye tracking system comprising at least two cameras configured to register eye images of at least one eye of a subject, causes the at least one processor to perform steps comprising:
    obtaining eye images from at least one camera in a subset of the at least two cameras;
    determining a first pupil parameter based on a first eye image of the eye images;
    determining a second pupil parameter based on a second eye image of the eye images;
    comparing the first pupil parameter and the second pupil parameter to one another to obtain a test parameter;
    check the test parameter against at least one operation criterion; and
    in response to checking the test parameter against the at least one operation criterion, assigning an operation state for at least one camera in the subset of the at least two cameras, wherein the operation state involves one of: (A) operating the camera at a high frame rate if the test parameter indicates that the eye image from the camera fulfills a first operation criterion, (B) operating the camera at a reduced frame rate being lower than the high frame rate if the test parameter indicates that the eye image from the camera fulfills a second operation criterion but not the first operation criterion, (C) the camera being in a standby mode if the test parameter indicates that the eye image from the camera fulfills a third operation criterion but neither the first operation criterion nor the second operation criterion, or (D) the camera being powered off if the test parameter indicates that the eye image from the camera does not fulfill any of the first operation criterion, the second operation criterion, or the third operation criterion.

11. A control unit for conserving energy in an eye tracking system comprising at least two cameras configured to register eye images of at least one eye of a subject, the control unit comprising:
    an input interface configured to obtain eye images from at least one camera in a subset of the at least two cameras;
    a processor configured to:
    determine a first pupil parameter based on a first eye image of the eye images;
    determine a second pupil parameter based on a second eye image of the eye images;
    compare the first pupil parameter and the second pupil parameters to one another to obtain a test parameter;
    check the test parameter against at least one operation criterion; and
    in response to checking the test parameter against the at least one operation criterion, assign a respective operation state to at least one camera in the subset of the at least two cameras, wherein the operation state involves one of: (A) operating the camera at a high frame rate if the test parameter indicates that the eye image from the camera fulfills a first operation criterion, (B) operating the camera at a reduced frame rate being lower than the high frame rate if the test parameter indicates that the eye image from the camera fulfills a second operation criterion but not the first operation criterion, (C) the camera being in a standby mode if the test parameter indicates that the eye image from the camera fulfills a third operation criterion but neither the first operation criterion nor the second operation criterion, or (D) the camera being powered off if the test parameter indicates that the eye image from the camera does not fulfill any of the first operation criterion, the second operation criterion, or the third operation criterion; and an output interface configured to forward the respective assigned operation state to the at least one camera.

12. The control unit of claim 11, wherein the subset contains a first camera, the processor further configured to:
obtain the first eye image captured by the first camera during a first time period; and
obtain the second eye image captured by the first camera during a second time period after the first time period,
wherein the test parameter comprises a measure expressing a difference between the first eye image and the second eye image.

13. The control unit of claim 11, wherein the subset contains a first camera and a second camera, the processor further configured to:
obtain the first eye image captured by the first camera during a first time period; and
obtain the second eye image captured by the second camera during the first time period,
wherein the test parameter comprises a measure expressing a difference between the first eye image and the second eye image.

14. The control unit of claim 13, wherein the first eye image and the second eye image are images of the same eye of the subject; and
wherein the first camera is configured to register the first eye image from a first angle relative to the same eye and the second camera is configured to register the second eye image from a second angle different from the first angle relative to the same eye.

15. The control unit of claim 11, wherein each of the first pupil parameter and the second pupil parameter expresses respective characteristics of a pupil of a subject in terms of one or more of a pupil size or a pupil position.

16. A head-mounted display comprising:
at least two cameras configured to register eye images of at least one eye of a subject; and
a control unit, comprising:
an input interface configured to obtain eye images from at least one camera in a subset of the at least two cameras;
a processor configured to:
determine a first pupil parameter based on a first eye image of the eye images;
determine a second pupil parameter based on a second eye image of the eye images;
compare the first pupil parameter and the second pupil parameter to one another to obtain a test parameter;
check the test parameter against at least one operation criterion; and
in response to checking the test parameter against the at least one operation criterion, assign a respective operation state to the at least one camera in the subset of the at least two cameras, wherein the operation state involves one of:
(A) operating the camera at a high frame rate if the test parameter indicates that the eye image from the camera fulfills a first operation criterion, (B) operating the camera at a reduced frame rate being lower than the high frame rate if the test parameter indicates that the eye image from the camera fulfills a second operation criterion but not the first operation criterion, (C) the camera being in a standby mode if the test parameter indicates that the eye image from the camera fulfills a third operation criterion but neither the first operation criterion nor the second operation criterion, or (D) the camera being powered off if the test parameter indicates that the eye image from the camera does not fulfill any of the first operation criterion, the second operation criterion, or the third operation criterion; and
an output interface configured to forward the respective assigned operation state to the at least one camera.

17. The head mounted display of claim 16, wherein the subset contains a first camera;
wherein the processor further configured to obtain the first eye image captured by the first camera during a first time period and obtain the second eye image captured by the first camera during a second time period after the first time period; and
wherein the test parameter comprises a measure expressing a difference between the first eye image and the second eye image.

18. The head mounted display of claim 16, wherein the subset contains a first camera and a second camera;
wherein the processor further configured to obtain the first eye image captured by the first camera during a first time period and obtain the second eye image captured by the second camera during the first time period; and
wherein the test parameter comprises a measure expressing a difference between the first and second eye images.

19. The head mounted display of claim 18, wherein the first eye image and the second eye image are images of the same eye of the subject; and
wherein the first camera is configured to register the first eye image from a first angle relative to the same eye and the second camera is configured to register the second eye image from a second angle different from the first angle relative to the same eye.

* * * * *